(12) United States Patent
Barron et al.

(10) Patent No.: US 12,194,168 B2
(45) Date of Patent: Jan. 14, 2025

(54) LIGHTING AND DISSIPATION DEVICE

(71) Applicant: Vyv, Inc., Latham, NY (US)

(72) Inventors: Robert Barron, Boulder, CO (US);
Cori Winslow, Rensselaer, NY (US);
James Peterson, Falls Church, VA (US)

(73) Assignee: Vyv, Inc., Latham, NY (US)

( * ) Notice: Subject to any disclaimer, the term of this patent is extended or adjusted under 35 U.S.C. 154(b) by 302 days.

(21) Appl. No.: 16/719,314

(22) Filed: Dec. 18, 2019

(65) Prior Publication Data

US 2020/0197550 A1 Jun. 25, 2020

Related U.S. Application Data

(60) Provisional application No. 62/782,232, filed on Dec. 19, 2018.

(51) Int. Cl.
| | | |
|---|---|---|
| *A61L 2/10* | (2006.01) | |
| *A61L 2/08* | (2006.01) | |
| *A61L 2/24* | (2006.01) | |
| *H05K 7/20* | (2006.01) | |

(52) U.S. Cl.
CPC .............. *A61L 2/10* (2013.01); *A61L 2/084* (2013.01); *A61L 2/24* (2013.01); *H05K 7/20145* (2013.01); *H05K 7/20154* (2013.01); *H05K 7/20172* (2013.01); *H05K 7/20209* (2013.01); *A61L 2202/11* (2013.01); *A61L 2202/14* (2013.01)

(58) Field of Classification Search
CPC .................................... A61L 2/24; A61L 2/10
See application file for complete search history.

(56) References Cited

U.S. PATENT DOCUMENTS

| | | |
|---|---|---|
| 1,493,820 A | 5/1924 | Miller et al. |
| 2,622,409 A | 12/1952 | Stimkorb |
| 2,773,715 A | 12/1956 | Lindner |
| 3,314,746 A | 4/1967 | Millar |
| 3,670,193 A | 6/1972 | Thorington et al. |

(Continued)

FOREIGN PATENT DOCUMENTS

| | | |
|---|---|---|
| CN | 1932370 A | 3/2007 |
| CN | 201396611 Y | 2/2010 |

(Continued)

OTHER PUBLICATIONS

Translation of KR 101895978 B1, 2018.*

(Continued)

*Primary Examiner* — Kevin Joyner
(74) *Attorney, Agent, or Firm* — Banner & Witcoff, Ltd.

(57) ABSTRACT

Systems, methods, and apparatuses involving lighting device dissipation are provided. An example light emitting device for inactivating microorganisms may comprise a vent configured to allow air to flow therethrough. The light emitting device may comprise a light emitter disposed on a substrate and configured to at least produce a light. The light may comprise a radiant flux sufficient to initiate inactivation of microorganisms, wherein at least 20% of a spectral energy of the light is in a wavelength in a range of 380-420 nanometers (nm). The light emitting device may comprise a fan configured to create an airflow through the vent and towards the substrate.

6 Claims, 6 Drawing Sheets

(56) References Cited

U.S. PATENT DOCUMENTS

| | | | |
|---|---|---|---|
| 3,791,864 | A | 2/1974 | Steingroever |
| 3,926,556 | A | 12/1975 | Boucher |
| 3,992,646 | A | 11/1976 | Corth |
| 4,121,107 | A | 10/1978 | Bachmann |
| 4,461,977 | A | 7/1984 | Pierpoint et al. |
| 4,576,436 | A | 3/1986 | Daniel |
| 4,867,052 | A | 9/1989 | Cipelletti |
| 4,892,712 | A | 1/1990 | Robertson et al. |
| 4,910,942 | A | 3/1990 | Dunn et al. |
| 5,231,472 | A | 7/1993 | Marcus et al. |
| 5,489,827 | A | 2/1996 | Xia |
| 5,505,912 | A * | 4/1996 | Hallett ............... B01J 19/123 422/906 |
| 5,530,322 | A | 6/1996 | Ference et al. |
| 5,559,681 | A | 9/1996 | Duarte |
| 5,668,446 | A | 9/1997 | Baker |
| 5,721,471 | A | 2/1998 | Begemann et al. |
| 5,725,148 | A | 3/1998 | Hartman |
| 5,800,479 | A | 9/1998 | Thiberg |
| 5,901,564 | A | 5/1999 | Comeau, II |
| 5,915,279 | A | 6/1999 | Cantrall et al. |
| 5,962,989 | A | 10/1999 | Baker |
| 5,968,766 | A | 10/1999 | Powers |
| 6,031,958 | A | 2/2000 | McGaffigan |
| 6,166,496 | A | 12/2000 | Lys et al. |
| 6,183,500 | B1 | 2/2001 | Kohler |
| 6,242,752 | B1 | 6/2001 | Soma et al. |
| 6,246,169 | B1 | 6/2001 | Pruvot |
| 6,251,127 | B1 | 6/2001 | Biel |
| 6,379,022 | B1 | 4/2002 | Amerson et al. |
| 6,477,853 | B1 | 11/2002 | Khorram |
| 6,524,529 | B1 | 2/2003 | Horton, III |
| 6,551,346 | B2 | 4/2003 | Crossley |
| 6,554,439 | B1 | 4/2003 | Teicher et al. |
| 6,627,730 | B1 | 9/2003 | Burnie |
| 6,676,655 | B2 | 1/2004 | McDaniel |
| 6,791,259 | B1 | 9/2004 | Stokes et al. |
| 6,902,807 | B1 | 6/2005 | Argoitia et al. |
| 7,015,636 | B2 | 3/2006 | Bolta |
| 7,175,807 | B1 | 2/2007 | Jones |
| 7,190,126 | B1 | 3/2007 | Paton |
| 7,198,634 | B2 | 4/2007 | Harth et al. |
| 7,201,767 | B2 | 4/2007 | Bhullar |
| 7,213,941 | B2 | 5/2007 | Sloan et al. |
| 7,438,719 | B2 | 10/2008 | Chung et al. |
| 7,476,885 | B2 | 1/2009 | Garcia et al. |
| 7,503,675 | B2 | 3/2009 | Demarest et al. |
| 7,516,572 | B2 | 4/2009 | Yang et al. |
| 7,521,875 | B2 | 4/2009 | Maxik |
| 7,611,156 | B2 | 11/2009 | Dunser |
| 7,612,492 | B2 | 11/2009 | Lestician |
| 7,658,891 | B1 | 2/2010 | Barnes |
| 7,955,695 | B2 | 6/2011 | Argoitia |
| 8,035,320 | B2 | 10/2011 | Sibert |
| 8,214,084 | B2 | 7/2012 | Ivey et al. |
| 8,232,745 | B2 | 7/2012 | Chemel et al. |
| 8,357,914 | B1 | 1/2013 | Caldwell |
| 8,398,264 | B2 | 3/2013 | Anderson et al. |
| 8,467,052 | B1 | 6/2013 | Chao et al. |
| 8,476,844 | B2 | 7/2013 | Hancock et al. |
| 8,481,970 | B2 | 7/2013 | Cooper et al. |
| 8,506,612 | B2 | 8/2013 | Ashdown |
| 8,508,204 | B2 | 8/2013 | Deurenberg et al. |
| 8,562,913 | B2 * | 10/2013 | Searle ............... A61L 9/16 422/121 |
| 8,761,565 | B1 | 6/2014 | Coleman et al. |
| 8,886,361 | B1 | 11/2014 | Harmon et al. |
| 8,895,940 | B2 | 11/2014 | Moskowitz et al. |
| 8,999,237 | B2 | 4/2015 | Tumanov |
| 9,024,276 | B2 | 5/2015 | Pugh et al. |
| 9,027,479 | B2 | 5/2015 | Raksha et al. |
| 9,028,084 | B2 | 5/2015 | Maeng et al. |
| 9,039,966 | B2 | 5/2015 | Anderson et al. |
| 9,046,227 | B2 | 6/2015 | David et al. |
| 9,078,306 | B2 | 7/2015 | Mans et al. |
| 9,119,240 | B2 | 8/2015 | Nagazoe |
| 9,173,276 | B2 | 10/2015 | Van Der Veen et al. |
| 9,257,059 | B2 | 2/2016 | Raksha et al. |
| 9,283,292 | B2 | 3/2016 | Kretschmann |
| 9,313,860 | B2 | 4/2016 | Wingren |
| 9,323,894 | B2 | 4/2016 | Kiani |
| 9,333,274 | B2 | 5/2016 | Peterson et al. |
| 9,368,695 | B2 | 6/2016 | David et al. |
| 9,410,664 | B2 | 8/2016 | Krames et al. |
| 9,420,671 | B1 | 8/2016 | Sugimoto et al. |
| 9,433,051 | B2 | 8/2016 | Snijder et al. |
| 9,439,271 | B2 | 9/2016 | Ku et al. |
| 9,439,989 | B2 | 9/2016 | Lalicki et al. |
| 9,492,576 | B1 | 11/2016 | Cudak et al. |
| 9,581,310 | B2 | 2/2017 | Wu et al. |
| 9,623,138 | B2 | 4/2017 | Pagan et al. |
| 9,625,137 | B2 | 4/2017 | Li et al. |
| 9,681,510 | B2 | 6/2017 | van de Ven |
| 10,806,812 | B2 | 10/2020 | Barron et al. |
| 2002/0074559 | A1 | 6/2002 | Dowling et al. |
| 2002/0122743 | A1 | 9/2002 | Huang |
| 2003/0009158 | A1 | 1/2003 | Perricone |
| 2003/0019222 | A1 | 1/2003 | Takahashi et al. |
| 2003/0023284 | A1 | 1/2003 | Gartstein et al. |
| 2003/0124023 | A1 | 7/2003 | Burgess et al. |
| 2003/0178632 | A1 | 9/2003 | Hohn et al. |
| 2003/0207644 | A1 | 11/2003 | Green et al. |
| 2003/0222578 | A1 | 12/2003 | Cok |
| 2003/0231485 | A1 | 12/2003 | Chien |
| 2004/0008523 | A1 | 1/2004 | Butler |
| 2004/0010299 | A1 | 1/2004 | Tolkoff et al. |
| 2004/0024431 | A1 | 2/2004 | Carlet |
| 2004/0039242 | A1 | 2/2004 | Tolkoff et al. |
| 2004/0047142 | A1 | 3/2004 | Goslee |
| 2004/0147984 | A1 | 7/2004 | Altshuler et al. |
| 2004/0147986 | A1 | 7/2004 | Baumgardner et al. |
| 2004/0158541 | A1 | 8/2004 | Notarianni et al. |
| 2004/0159039 | A1 | 8/2004 | Yates et al. |
| 2004/0162596 | A1 | 8/2004 | Altshuler et al. |
| 2004/0230259 | A1 | 11/2004 | Di Matteo |
| 2004/0262595 | A1 | 12/2004 | Mears et al. |
| 2004/0266546 | A1 | 12/2004 | Huang |
| 2005/0055070 | A1 | 3/2005 | Jones et al. |
| 2005/0104059 | A1 | 5/2005 | Friedman et al. |
| 2005/0107849 | A1 | 5/2005 | Altshuler et al. |
| 2005/0107853 | A1 | 5/2005 | Krespi et al. |
| 2005/0159795 | A1 | 7/2005 | Savage et al. |
| 2005/0207159 | A1 | 9/2005 | Maxik |
| 2005/0212397 | A1 | 9/2005 | Murazaki et al. |
| 2005/0253533 | A1 | 11/2005 | Lys et al. |
| 2005/0267233 | A1 | 12/2005 | Joshi |
| 2006/0006678 | A1 | 1/2006 | Herron |
| 2006/0009822 | A1 | 1/2006 | Savage et al. |
| 2006/0022582 | A1 | 2/2006 | Radkov |
| 2006/0071589 | A1 | 4/2006 | Radkov |
| 2006/0085052 | A1 | 4/2006 | Feuerstein et al. |
| 2006/0138435 | A1 | 6/2006 | Tarsa et al. |
| 2006/0186377 | A1 | 8/2006 | Takahashi et al. |
| 2006/0230576 | A1 | 10/2006 | Meine |
| 2006/0247741 | A1 | 11/2006 | Hsu et al. |
| 2006/0262545 | A1 | 11/2006 | Piepgras et al. |
| 2007/0023710 | A1 | 2/2007 | Tom et al. |
| 2007/0061050 | A1 | 3/2007 | Hoffknecht |
| 2007/0115665 | A1 | 5/2007 | Mueller et al. |
| 2007/0164232 | A1 | 7/2007 | Rolleri et al. |
| 2007/0208395 | A1 | 9/2007 | Leclerc et al. |
| 2007/0258851 | A1 | 11/2007 | Fogg et al. |
| 2008/0008620 | A1 | 1/2008 | Alexiadis |
| 2008/0015560 | A1 | 1/2008 | Gowda et al. |
| 2008/0091250 | A1 | 4/2008 | Powell |
| 2008/0151533 | A1 | 6/2008 | Genova |
| 2008/0278927 | A1 | 11/2008 | Li et al. |
| 2008/0305004 | A1 | 12/2008 | Anderson et al. |
| 2008/0307818 | A1 | 12/2008 | Min et al. |
| 2009/0018621 | A1 | 1/2009 | Vogler et al. |
| 2009/0034236 | A1 | 2/2009 | Reuben |
| 2009/0076115 | A1 | 3/2009 | Wharton et al. |
| 2009/0154167 | A1 | 6/2009 | Lin |
| 2009/0231832 | A1 | 9/2009 | Zukauskas et al. |

(56) References Cited

U.S. PATENT DOCUMENTS

| | | |
|---|---|---|
| 2009/0262515 A1 | 10/2009 | Lee et al. |
| 2009/0285727 A1 | 11/2009 | Levy |
| 2009/0314308 A1 | 12/2009 | Kim et al. |
| 2010/0001648 A1 | 1/2010 | De Clercq et al. |
| 2010/0027259 A1 | 2/2010 | Simon et al. |
| 2010/0071257 A1 | 3/2010 | Tsai |
| 2010/0090935 A1 | 4/2010 | Tseng et al. |
| 2010/0102252 A1 | 4/2010 | Harmon et al. |
| 2010/0107991 A1 | 5/2010 | Elrod et al. |
| 2010/0121420 A1 | 5/2010 | Fiset et al. |
| 2010/0148083 A1 | 6/2010 | Brown et al. |
| 2010/0179469 A1 | 7/2010 | Hammond et al. |
| 2010/0232135 A1 | 9/2010 | Munehiro et al. |
| 2010/0246169 A1 | 9/2010 | Anderson et al. |
| 2011/0063835 A1 | 3/2011 | Rivas et al. |
| 2011/0084614 A1 | 4/2011 | Eisele et al. |
| 2011/0256019 A1 | 10/2011 | Gruen et al. |
| 2011/0316025 A1 | 12/2011 | Kuzuhara et al. |
| 2012/0014538 A1 | 1/2012 | Bozkurt et al. |
| 2012/0025717 A1 | 2/2012 | Klusmann et al. |
| 2012/0043552 A1 | 2/2012 | David et al. |
| 2012/0161170 A1 | 6/2012 | Dubuc et al. |
| 2012/0199005 A1 | 8/2012 | Koji et al. |
| 2012/0273340 A1 | 11/2012 | Felix |
| 2012/0280147 A1 | 11/2012 | Douglas |
| 2012/0281408 A1 | 11/2012 | Owen et al. |
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Hussell et al. |
| 2013/0181246 A1 | 7/2013 | Wu |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2013/0323375 A1 | 12/2013 | Takahashi et al. |
| 2014/0043810 A1* | 2/2014 | Jo .................... F21V 29/83 362/373 |
| 2014/0061509 A1 | 3/2014 | Shur et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0265868 A1 | 9/2014 | Morrisseau |
| 2014/0301062 A1 | 10/2014 | David et al. |
| 2014/0328046 A1 | 11/2014 | Aanegola et al. |
| 2014/0334137 A1 | 11/2014 | Hasenoehrl et al. |
| 2014/0362523 A1 | 12/2014 | Degner et al. |
| 2015/0049459 A1 | 2/2015 | Peeters et al. |
| 2015/0062892 A1 | 3/2015 | Krames et al. |
| 2015/0068292 A1 | 3/2015 | Su et al. |
| 2015/0086420 A1 | 3/2015 | Trapani |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1 | 8/2015 | Dross et al. |
| 2015/0233536 A1 | 8/2015 | Krames et al. |
| 2015/0273093 A1 | 10/2015 | Holub et al. |
| 2016/0000950 A1 | 1/2016 | Won |
| 2016/0000953 A1 | 1/2016 | Bettles et al. |
| 2016/0015840 A1 | 1/2016 | Gordon |
| 2016/0030609 A1 | 2/2016 | Peterson et al. |
| 2016/0030610 A1 | 2/2016 | Peterson et al. |
| 2016/0091172 A1 | 3/2016 | Wu et al. |
| 2016/0114067 A1 | 4/2016 | Dobrinsky et al. |
| 2016/0114186 A1 | 4/2016 | Dobrinsky et al. |
| 2016/0137528 A1 | 5/2016 | Wipprich |
| 2016/0168384 A1 | 6/2016 | Guidolin et al. |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0346565 A1 | 12/2016 | Rhodes et al. |
| 2016/0349179 A1 | 12/2016 | Rochette et al. |
| 2016/0354502 A1 | 12/2016 | Simmons et al. |
| 2016/0366745 A1 | 12/2016 | Hikmet et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0030555 A1 | 2/2017 | Lalicki et al. |
| 2017/0081874 A1 | 3/2017 | Daniels |
| 2017/0094960 A1 | 4/2017 | Sasaki et al. |
| 2017/0100494 A1 | 4/2017 | Dobrinsky et al. |
| 2017/0100607 A1 | 4/2017 | Pan et al. |
| 2017/0281812 A1 | 10/2017 | Dobrinsky et al. |
| 2017/0296691 A1* | 10/2017 | Kirschman ............... A61L 2/26 |
| 2017/0368210 A1 | 12/2017 | David et al. |
| 2018/0043044 A1 | 2/2018 | Hachiya et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0117194 A1 | 5/2018 | Dobrinsky et al. |
| 2018/0124883 A1 | 5/2018 | Bailey |
| 2018/0139817 A1 | 5/2018 | Yamakawa et al. |
| 2018/0180226 A1 | 6/2018 | Van Bommel et al. |
| 2018/0185533 A1 | 7/2018 | Lalicki et al. |
| 2018/0190625 A1 | 7/2018 | Steckel et al. |
| 2018/0280723 A1 | 10/2018 | Enwemeka et al. |
| 2018/0311386 A1 | 11/2018 | Hawkins et al. |
| 2018/0320872 A1 | 11/2018 | Weeks, Jr. et al. |
| 2019/0070323 A1 | 3/2019 | Atreya et al. |
| 2019/0368936 A1 | 12/2019 | Xu et al. |
| 2019/0371978 A1 | 12/2019 | Iwasa et al. |

FOREIGN PATENT DOCUMENTS

| | | |
|---|---|---|
| CN | 201423033 Y | 3/2010 |
| CN | 102213382 A | 10/2011 |
| CN | 103227225 A | 7/2013 |
| CN | 203436596 U | 2/2014 |
| CN | 105304801 A | 2/2016 |
| CN | 105339094 A | 2/2016 |
| CN | 105449081 A | 3/2016 |
| CN | 205360038 U | 7/2016 |
| CN | 106937461 A | 7/2017 |
| CN | 107575849 A | 1/2018 |
| CN | 107896505 A | 4/2018 |
| CN | 107921161 A | 4/2018 |
| DE | 102011001097 A1 | 9/2012 |
| DE | 102015207999 A1 | 11/2016 |
| DE | 102016009175 A1 | 2/2017 |
| EP | 0306301 A1 | 3/1989 |
| EP | 1693016 A1 | 8/2006 |
| EP | 1887298 A1 | 2/2008 |
| EP | 1943880 B1 | 4/2013 |
| FR | 2773715 A1 | 7/1999 |
| JP | 3090065 U | 11/2002 |
| JP | 2003-332620 A | 11/2003 |
| JP | 2003339845 A | 12/2003 |
| JP | 2004261595 A | 9/2004 |
| JP | 2004275927 A | 10/2004 |
| JP | 2007511279 A | 5/2007 |
| JP | 2008-004948 A | 1/2008 |
| JP | 2009-004351 A | 1/2009 |
| JP | 2011-513996 A | 4/2011 |
| JP | 2013-045896 A | 3/2013 |
| JP | 2013-093311 A | 5/2013 |
| JP | 2015-015106 A | 1/2015 |
| JP | 2015-035373 A | 2/2015 |
| JP | 2015174026 A | 10/2015 |
| JP | 2018525848 A | 9/2018 |
| JP | 2018533400 A | 11/2018 |
| KR | 20130096965 A | 9/2013 |
| KR | 101526261 B1 | 6/2015 |
| KR | 20160021100 A | 2/2016 |
| KR | 101648216 B1 | 8/2016 |
| KR | 20160127469 A | 11/2016 |
| KR | 101799538 B1 | 11/2017 |

(56) References Cited

FOREIGN PATENT DOCUMENTS

| | | | | | |
|---|---|---|---|---|---|
| KR | 20180036728 | A | | 4/2018 | |
| KR | 101895978 | B1 | * | 10/2018 | .......... F21V 33/0088 |
| TW | M268106 | U | | 6/2005 | |
| TW | 201412240 | A | | 4/2014 | |
| TW | 201604490 | A | | 2/2016 | |
| TW | 201611849 | A | | 4/2016 | |
| TW | M530654 | U | | 10/2016 | |
| TW | 201711707 | A | | 4/2017 | |
| TW | 201831977 | A | | 9/2018 | |
| TW | 201936226 | A | | 9/2019 | |
| WO | 0114012 | A1 | | 3/2001 | |
| WO | 03037504 | A1 | | 5/2003 | |
| WO | 2003035118 | A2 | | 5/2003 | |
| WO | 03063902 | A2 | | 8/2003 | |
| WO | 03084601 | A2 | | 10/2003 | |
| WO | 03089063 | A1 | | 10/2003 | |
| WO | 2004033028 | A2 | | 4/2004 | |
| WO | 2005048811 | A2 | | 6/2005 | |
| WO | 2005049138 | A1 | | 6/2005 | |
| WO | 2006023100 | A1 | | 3/2006 | |
| WO | 2006100303 | A2 | | 9/2006 | |
| WO | 2006126482 | A1 | | 11/2006 | |
| WO | 2007012875 | A1 | | 2/2007 | |
| WO | 2007035907 | A2 | | 3/2007 | |
| WO | 2008071206 | A1 | | 6/2008 | |
| WO | 2009056838 | A1 | | 5/2009 | |
| WO | 2010110652 | A1 | | 9/2010 | |
| WO | 2014097089 | A1 | | 6/2014 | |
| WO | 2015066099 | A2 | | 5/2015 | |
| WO | 2015189112 | A1 | | 12/2015 | |
| WO | 2016019029 | A1 | | 2/2016 | |
| WO | 2016068285 | A1 | | 5/2016 | |
| WO | 2016209632 | A1 | | 12/2016 | |
| WO | 2017009534 | A1 | | 1/2017 | |
| WO | 2017205578 | A1 | | 11/2017 | |
| WO | WO-2018090131 | A1 | * | 5/2018 | ........... A61N 5/0603 |
| WO | 2019108432 | A1 | | 6/2019 | |

OTHER PUBLICATIONS

Mar. 18, 2020—(WO) ISR & WO—App PCT/US2019/068799.
Oct. 31, 2008—(WO) ISR & WO—App PCT/GB2008/003679 (Univ Strathclyde).
May 4, 2010—(WO) IPRP—App PCT/GB2008/003679 (Univ Strathclyde).
Apr. 3, 2020—(WO) ISR & WO—App PCT/US2019/67444.
Jun. 1, 2020—(GB) Examiner's Report—App GB1802648.4.
Apr. 14, 2020—(TW) 2nd Office Action—App 107143577 (w/translation).
May 12, 2020—(JP) Final Office Action—JP 2018-525520.
Jun. 18, 2020—(WO) IPRP & WO—App PCT/US2018/061859.
Jul. 6, 2020—(WO) ISR & WO—App PCT/US2019/068799.
Jul. 23, 2020—(TW) Office Action w/TR—TW 108148627.
Nov. 28, 2020—(WO) ISR & WO—App PCT/US2020/051254.
Nov. 23, 2020—(WO) ISR & WO—App PCT/US2020/051254.
Nov. 6, 2020—(TW) Office Action w/Tr.—TW 108146777.
Dec. 2, 2020—(TW) Rejection Decision—App 108111242 (Eng Trans).
Sep. 29, 2020—(WO) ISR & WO—App PCT/US2020/046504.
Gillespie et al., "Development of an antimicrobial blended white LED system containing pulsed 405nm LEDs for decontamination applications," Progress in Biomedical Optics and Imaging, SPIE—International Society for Optical Engineering, Bellingham, WA, vol. 10056, Mar. 14, 2017, pp. 100560Y-100560Y, XP060084045, whole document.
Maclean et al., "Inactivation of Bacterial Pathogens following Exposure to Light from a 405-Nanometer Light-Emitting Diode Array," Applied and Environmental Microbiology, vol. 75, No. 7, Apr. 2009, pp. 1932-1937, 6 pages.
Nov. 15, 2021—(CA) Office Action—CA 3095579.
Jul. 21, 2021—(TW) Office Action—TW 108148627.
Aug. 31, 2021—(CN) Office Action—CN 201980033309.1.
Sep. 21, 2021—(JP) Office Action—2020-154129.
Oct. 21, 2021—(TW) Office Action—TW 109132488 w/Trn.
Oct. 20, 2016—(WO) ISR & WO—App PCT/US2016/44634, 7 pages.
Nov. 2, 2015—(WO) WO & ISR—App PCT/US2015/042678.
May 4, 2010—(WO) IPRP—App PCT/GB2008/003679.
Oct. 31, 2008—(WO) ISR & WO—App PCT/GB2008/003679.
Jun. 29, 2018—(DE) Office Action—App 112016003453.9.
Mar. 6 2018—(WO) ISR & WO—App PCT/US2017/068749.
Apr. 16, 2018—(WO) ISR & WO—App PCT/US2017/068755.
Nov. 27, 2018—(JP) Office Action—JP 2018-525520.
Jan. 4, 2019—(TW) Office Action—App 104124977.
Feb. 11, 2019—(WO) ISR—App PCT/US2018/061859.
Feb. 28, 2019—(WO) ISR—App PCT/US2018/061843.
Feb. 28, 2019—(WO) ISR & WO—App PCT/US2018/061856.
Apr. 15, 2019—(CA) Examiner's Report—App 2,993,825.
Jul. 8, 2019—(WO) ISR & WO—App PCT/US2019/024593.
Nov. 5, 2019—(JP) Final Office Action—JP 2018-525520.
Oct. 9, 2019—(CN) Office Action—CN 201680048598.9.
Oct. 1, 2019—(KR) Office Action—App 10-2018-7005077—Eng Tran.
Apr. 15, 2019—(CA) Office Action—App 2,993,825.
Nov. 20, 2019—(CA) Examiner's Report—App 2,993,825.
Dec. 26, 2019—(TW) Office Action and Search Report—App 107143161.
Dec. 27, 2019—(TW) Office Action and Search Report—App 108111242.
Sep. 6, 2019—(TW) Office Action—App 107143162.
Sep. 20, 2019—(TW) Office Action—App 107143577.
Aug. 2, 2022—(JP) Office Actio—App. No. 2021-536288.
Jun. 28, 2022—(EP) Communication pursuant to Article 94(3)—App. No. 19842661.1-1101.
Jul. 20, 2022—(CN) First Office Action—App. No. 201980084506.6.
Sep. 29, 2022—(CA) Examiner's Report—App. No. 3,122,597.
Jun. 28, 2022—(EP) Office Action—App. No. 19842661.1-1101.
May 16, 2023—(EP) Summons to attend oral proceedings pursuant to Rule 115(1) EPC—App. No. 19842661.1.
Jun. 23, 2023—(CA) Office Action—App. No. 3123597.
Mar. 5, 2024—(JP) Notice of Final Rejection—JP 10-2021-7022859.
Nov. 12, 2023—(IL) Office Action—App No. 283962.
Jul. 24, 2023 (KR) Office Action—App. No. 2021-7022859.

* cited by examiner

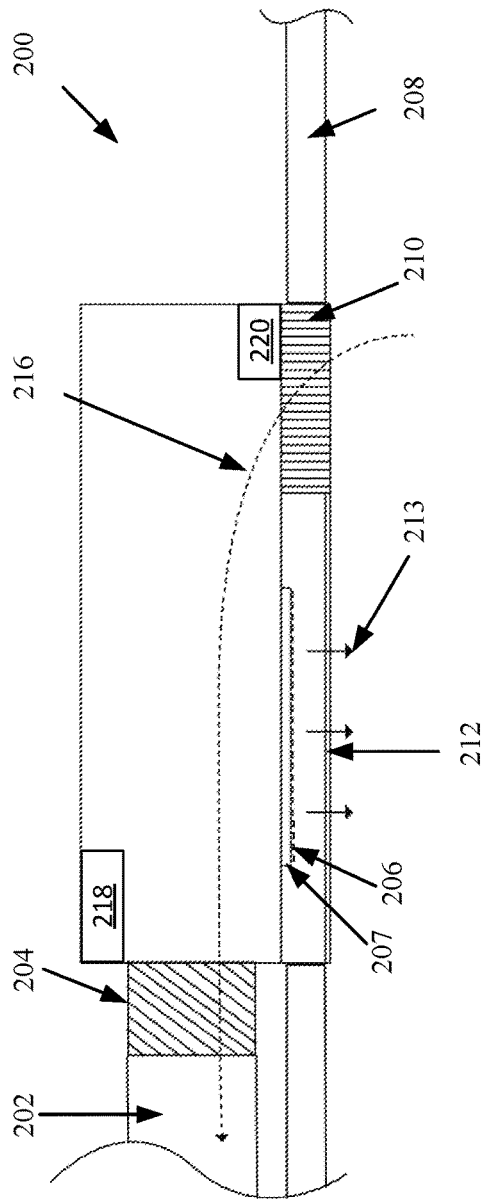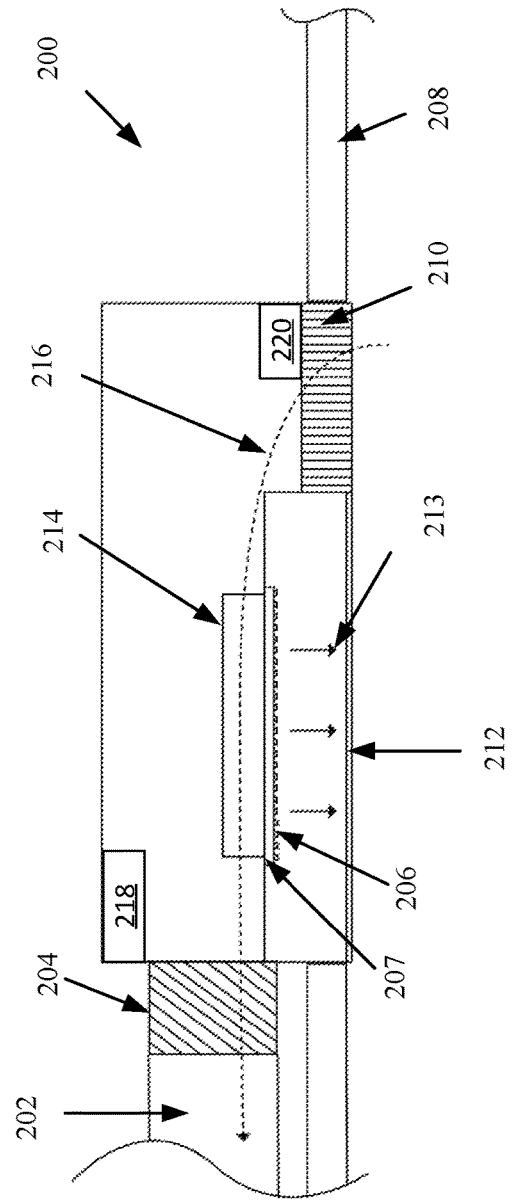
FIG. 2A
FIG. 2B

LIGHTING AND DISSIPATION DEVICE

CROSS REFERENCE TO RELATED APPLICATIONS

This application claims the benefit of U.S. Provisional Application No. 62/782,232, titled "Lighting and Dissipation Device," and filed on Dec. 19, 2018. The above-referenced application is hereby incorporated by reference in its entirety.

TECHNICAL FIELD

Aspects of the present disclosure generally relate to processes, systems, and apparatus for a disinfecting lighting and dissipation device.

BACKGROUND

Bacterial disinfection and/or microorganism inactivation may be beneficial for human health. Such disinfection and inactivation may increase both personal and environmental hygiene. Many bacterial disinfection and/or microorganism inactivation methods may be employed to improve human health factors. For example, sickness, infection, and/or bacterial or microorganism contamination (e.g., through the many modes of intake into the human body) in an environment may be prevented or otherwise hindered by bacterial disinfection and/or microorganism inactivation.

Furthermore, bacterial disinfection and/or microorganism inactivation may reduce mold, mildew, and odor causing bacteria that may be affecting bathrooms, kitchens, and basements, and causing undesirable visual effects and malodor. Some types of mold that can grow in spaces occupied by humans may have negative effects on human health.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

In some examples, a light emitting system may provide lighting and/or disinfection in combination with an exhaust, e.g., exterior exhaust or internal circulation exhaust system. In some examples, the light emitting system may comprise one or more light emitters such as, for example, light emitting diodes (LEDs).

In some examples, a light emitting device for inactivating microorganisms may comprise a vent configured to allow air to flow therethrough. The light emitting device may comprise a light emitter disposed on a substrate and configured to at least produce a light comprising a radiant flux sufficient to initiate inactivation of microorganisms, wherein at least 20% of a spectral energy of the light is in a wavelength range of 380-420 nanometers (nm). The light emitting device may comprise a fan configured to create an airflow through the vent and towards the substrate.

In some examples, a light emitting system may comprise a light source configured to emit a light comprising at least 20% of a spectral energy of the light in a wavelength range of 380-420 nanometers (nm) and a radiant flux sufficient to initiate inactivation of microorganisms. The light emitting system may comprise a fan configured to create an airflow through the light emitting system. The light emitting system may comprise a sensor configured to measure a temperature associated with the light source. The light emitting system may comprise a controller in communication with the light source, the fan, and the sensor. The controller may be configured to adjust, based on the temperature associated with the light source, an airflow characteristic.

In some examples, a method may comprise outputting, via a light emitter, a light comprising at least 20% of a spectral energy of the light in a wavelength a range of 380-420 nanometers (nm) and a radiant flux sufficient to initiate inactivation of microorganisms. The method may comprise sensing, via a sensor, a temperature associated with the light emitter. The method may comprise adjusting, based on the temperature associated with the light emitter, an output of the light emitter. The method may comprise adjusting, based on the temperature associated with the light emitter, an airflow created by a fan.

BRIEF DESCRIPTION OF THE DRAWINGS

FIGS. 2A-2B show example light emitting systems including a light emitter and an exhaust system in accordance with examples of the present disclosure.

DETAILED DESCRIPTION

Figure 1:
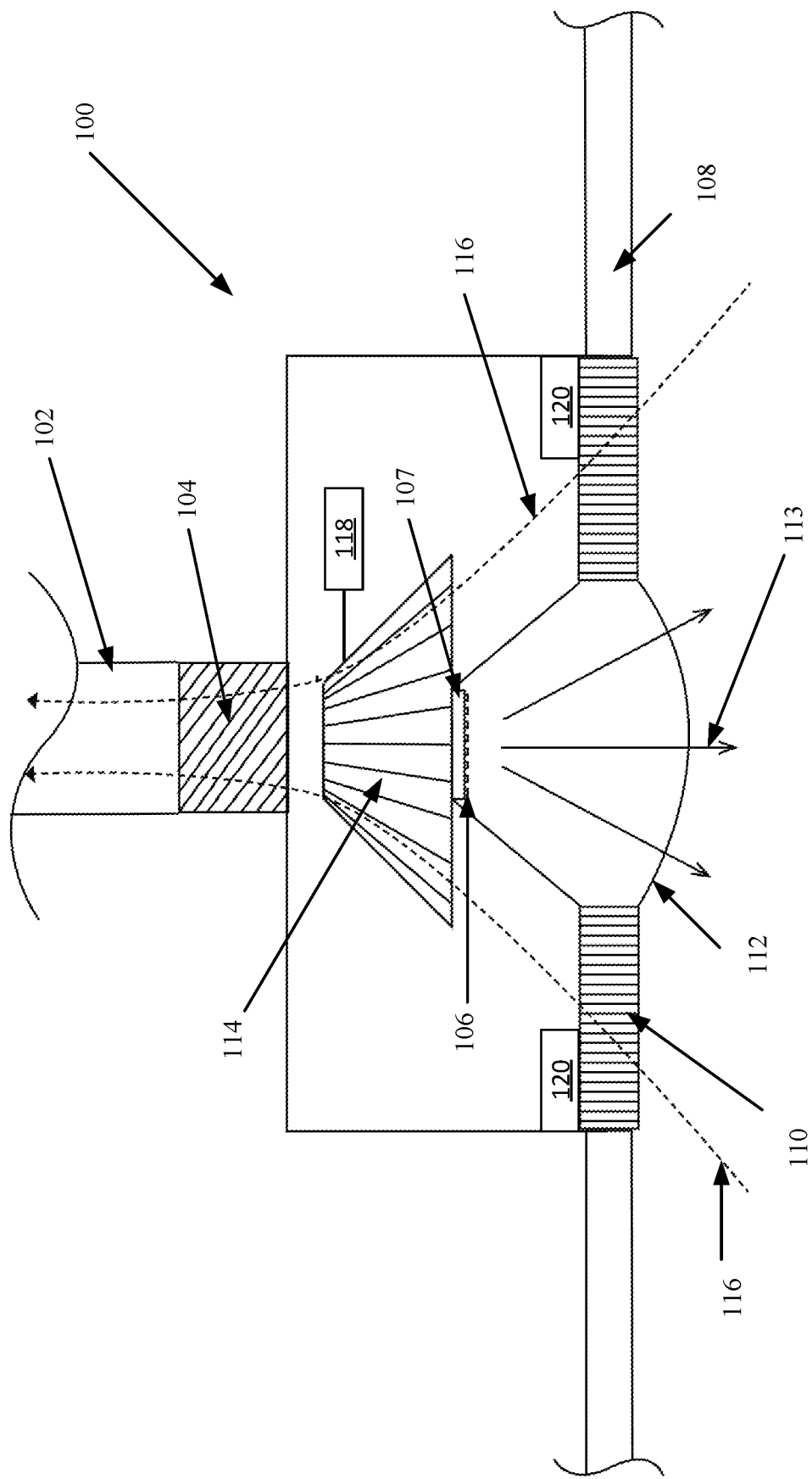
FIG. 1 shows an example light emitting system including a light emitter and an exhaust system in accordance with an example of the present disclosure.

In the following description of the various embodiments, reference may be made to the accompanying drawings, which form a part hereof, and in which may be shown by way of illustration, various embodiments of the disclosure that may be practiced. It may be understood that other embodiments may be utilized.

Residential and commercial spaces, such as bathrooms, may be disinfected in a number of ways. One technique may be cleaning with disinfecting chemical cleaners or soaps. Chemical cleaners may provide only intermittent disinfection, and may allow harmful microorganisms to build up between cleanings. Some disinfecting systems may transmit ultraviolet (UV) light onto surfaces for disinfection. UV light exposure may be harmful for humans and animals, so UV light should be off when there may be a chance of user exposure. Accordingly, these systems may involve complex controls to prevent harmful, direct exposure to humans. UV light may also cause degradation and yellowing of material (e.g., plastic) and/or surfaces.

Wavelengths of visible light in the violet range, 380-420 nanometer (nm) (e.g., 405 nm), may have a lethal effect on microorganisms such as bacteria, yeast, mold, and fungi. For example, *Escherichia coli* (*E. coli*), *Salmonella*, Methicillin-resistant *Staphylococcus aureus* (MRSA), and *Clostridium difficile* may be susceptible to 380-420 nm light. Such wavelengths may initiate a photoreaction with porphyrin molecules found in microorganisms. The porphyrin molecules may be photoactivated and may react with other cellular components to produce Reactive Oxygen Species (ROS). ROS may cause irreparable cell damage and eventually destroy, kill, or otherwise inactivate the cell. Because humans, plants, and/or animals do not contain the same porphyrin molecules, this technique may be completely safe for human exposure.

In some examples, inactivation, in relation to microorganism death, may include control and/or reduction in microorganism colonies or individual cells when exposed to disinfecting light for a certain duration. Light may be utilized for the inactivation of bacterial pathogens with a peak wavelength of light, or in some examples, multiple peak wavelengths, in a range of approximately 380 nm to 420 nm. For example, approximately 405 nm light may be used as the peak wavelength. It should be understood that any wavelength within 380 nm to 420 nm may be utilized, and that the peak wavelength may include a specific wavelength plus or minus approximately 5 nm. Other values and ranges disclosed herein may be used within plus or minus approximately 10% of the disclosed values.

Radiant flux (e.g., radiant power, radiant energy), measured in Watts, is the total power from a light source. Irradiance is the power per unit area at a distance away from the light source. In some examples, the target irradiance on a target surface from the light source may be 10 mW/cm$^2$. A 10 mW/cm$^2$ target irradiance may be provided, for example, by a light source with a radiant flux of 10 mW located 1 cm from the target surface. In another example, a light source may be located 5 cm from the target surface. With a target irradiance of 10 mW/cm$^2$, the light source may be configured to produce a radiant flux approximately 250 mW. These calculations may be approximately based on the inverse square law, as shown in Equation 1, where the excitation light source may be assumed to be a point source, E is the irradiance, I is the radiant flux, and r is the distance from the excitation light source to a target surface.

$$E \cong \frac{I}{r^2} \quad \text{Equation 1}$$

A minimum irradiance of light (e.g., in the 380-420 nm wavelength) on a surface may cause microbial inactivation. For example, a minimum irradiance of 0.02 milliwatts per square centimeter (mW/cm$^2$) may cause microbial inactivation on a surface over time. A minimum irradiance of 0.02 mW/cm$^2$, for example, may be provided by a light source with a radiant flux of 0.02 mW located 1 cm from the target surface. In some examples, an irradiance of 0.05 mW/cm$^2$ may inactivate microorganisms on a surface, but higher values such as, for example, 0.1 mW/cm$^2$, 0.5 mW/cm$^2$, or 1 mW/cm$^2$ may be used for quicker microorganism inactivation. In some examples, even higher irradiances may be used. The irradiance of light on the surface may be changed by changing the radiant flux of the light source or changing the distance from the light source to the target surface.

Dosage (measured in Joules/cm$^2$) may be another metric for determining an appropriate irradiance for microbial inactivation over a period of time. Table 1 below shows example correlations between irradiance in mW/cm$^2$ and Joules/cm$^2$ based on different exposure times. These values are examples and many others may be possible.

TABLE 1

| Irradiance (mW/cm$^2$) | Exposure Time (hours) | Dosage (Joules/cm$^2$) |
|---|---|---|
| 0.02 | 1 | 0.072 |
| 0.02 | 24 | 1.728 |
| 0.02 | 250 | 18 |
| 0.02 | 500 | 36 |
| 0.02 | 1000 | 72 |
| 0.05 | 1 | 0.18 |
| 0.05 | 24 | 4.32 |
| 0.05 | 250 | 45 |
| 0.05 | 500 | 90 |
| 0.05 | 1000 | 180 |
| 0.1 | 1 | 0.36 |
| 0.1 | 24 | 8.64 |
| 0.1 | 250 | 90 |
| 0.1 | 500 | 180 |
| 0.1 | 1000 | 360 |
| 0.5 | 1 | 1.8 |
| 0.5 | 24 | 43.2 |
| 0.5 | 250 | 450 |
| 0.5 | 500 | 900 |
| 0.5 | 1000 | 1800 |
| 1 | 1 | 3.6 |
| 1 | 24 | 86.4 |
| 1 | 250 | 900 |
| 1 | 500 | 1800 |
| 1 | 1000 | 3600 |

Table 2 shows the different dosages recommended for the inactivation of different bacterial species using narrow spectrum 405 nm light. Inactivation being measured by $Log_{10}$ reduction. Example dosages and other calculations shown herein may be examples from laboratory settings, and may not represent example dosages or calculations in other situations. For example, real world applications may require dosages or other calculations performed herein that may differ from example laboratory data. Other dosages of 405 nm light may be used with other bacteria not listed below.

TABLE 2

| Organism | Recommended Dose (J/cm$^2$) for 1-Log Reduction in Bacteria |
|---|---|
| *Staphylococcus aureus* | 20 |
| MRSA | 20 |
| *Pseudomonas aeruginosa* | 45 |
| *Escherichia coli* | 80 |
| *Enterococcus faecalis* | 90 |

Equation 2 may be used in order to determine irradiance, dosage, or time using one or more data points from Table 1 and Table 2:

$$\frac{\text{Irradiance}\left(\frac{mW}{cm^2}\right)}{1000} * \text{Time (s)} = \text{Dosage}\left(\frac{J}{cm^2}\right) \quad \text{Equation 2}$$

Irradiance may be determined based on dosage and time. For example, if a dosage of 30 Joules/cm$^2$ is required and the object desired to be disinfected is exposed to light overnight for 8 hours, the irradiance may be approximately 1 mW/cm$^2$. The example 1 mW/cm$^2$ irradiance may be provided, for example, by a 1 mW light source located 1 cm away from the target surface. If a dosage of 50 Joules/cm$^2$ is required and the object desired to be disinfected is exposed to light for 48 hours, a smaller irradiance of only approximately 0.3 mW/cm$^2$ may be sufficient.

Time may be determined based on irradiance and dosage. For example, a device may be configured to emit an irradiance of disinfecting energy (e.g., 0.05 mW/cm$^2$) and a target bacteria may require a dosage of 20 Joules/cm$^2$ to kill the target bacteria. Disinfecting light at 0.05 mW/cm$^2$ may have a minimum exposure time of approximately 4.6 days to achieve the dosage of 20 Joules/cm$^2$. Dosage values may be determined by a target reduction in bacteria. Once the bacteria count is reduced to a desired amount, disinfecting light may be continuously applied to keep the bacteria counts down. Disinfecting light may be continuously applied to prevent or reduce bacteria and/or microorganism growth.

Different colors of light may be utilized with a percentage (e.g., 20%) of their spectral power distribution within the wavelength range of 380-420 nanometers. For example, a white light containing light across the visible light spectrum from 380-750 nanometers, may be used for disinfection purposes, with at least 20% of its energy within the wavelength range of 380-420 nm. In some examples, various colors of light may be utilized with a percentage of 30% to 80% spectral power distribution within the wavelength range of 380-420 nm.

Light emitting (e.g., LED based) systems for lighting or disinfection generate heat that should be dissipated away from components to prevent loss of efficiency, increase lifetime, and improve installation fire safety considerations. Heat sinks, heat pipes, or forced air may be used for thermal dissipation.

In residential, institutional, or commercial design, an exhaust fan may be incorporated into the ceiling to exhaust air from the room environment. The exhaust mechanism may remove odors, steam, humidity, or additional undesirable airborne particles or gasses. Kitchen range hoods may include exhaust fans. Such exhaust systems may sometimes be independent from lighting and/or disinfection systems.

In some examples (e.g., ventilation/light combinations such as range hoods or bathroom fans), light emitting systems may be exposed to moist air. In some such examples, lighting portions of the system may be separated and/or sealed from air handling portions. In sealed systems, excess heat may be generated and performance may be reduced. In some examples, lighting portions may be separated from air handing portions due to potential hazards from fumes, explosions, fire, or LED material incompatibility (e.g., Volatile Organic Compounds).

Configurations of light emitting system disclosed herein may save energy as compared to separate exhaust systems and disinfecting light systems. The proposed light emitting system may advantageously provide energy saving, for example, by utilizing a fan for both exhaust (e.g., exhaust heat, contaminants, etc.) and cooling of a light emitting system.

As illustrated in FIG. 1, a light emitting (e.g., LED based) system 100 may be provided. The light emitting system 100 may provide lighting and/or disinfection. The light emitting system 100 may include an exhaust 102 and an exhaust fan 104, which may yield synergistic benefits from using existing forced air currents of exhaust as forced air cooling for the lighting and/or disinfection systems. The exhaust 102 and/or exhaust fan 104 may comprise an external or internal circulation system. The light emitting system 100 may further comprise one or more light emitter(s) 106. The one or more light emitter(s) may be populated on a substrate 107. The substrate 107 may comprise a printed circuit board (PCB), such as, for example, a fiberglass, epoxy resin, copper, tin-lead, gold, and/or aluminum PCB. The one or more light emitter(s) 106 may be configured to emit light 113 with at least a portion thereof in the wavelength range of 380-420 nm (e.g., 405 nm) and with a radiant flux sufficient to provide an irradiance and/or dosage sufficient to initiate inactivation or bacteria and/or microorganisms. The light emitter(s) 106 may be configured in accordance with Tables 1 and 2 and Equation 1 disclosed above. The light emitter(s) 106 may be adjusted, via a control system 118, to vary radiant flux, irradiance, time, and/or dosage in order to inactivate bacterial and/or microorganisms as disclosed herein.

In some examples, the exhaust 102 and/or exhaust fan 104 may be configured to provide thermal dissipation of forced air without the increased component or energy dissipation required of a forced air-cooled lighting and/or disinfection system. In some examples, energy consumption may be reduced, because any energy consumed for the exhaust 102 and/or exhaust fan 104 may be used for multiple purposes (e.g., air removal and/or cooling the light emitting system). In some examples, the exhaust 102 and/or exhaust fan 104 may be configured to lower the temperature of (e.g., cool) the light emitter(s) 106 (e.g., LEDs), or the substrate 107, in the light emitting system 100 below normal operating temperatures. For example, normal operating temperatures may correspond to the temperature that the light emitter(s) 106 would reach when operating in a non-ventilated system using similar power conditions.

Rather than merely dissipate heat generated by the light emitter(s) 106, the exhaust 102 and/or exhaust fan 104 may be configured to lower the temperatures of the light emitter(s) 106 below normal operating temperatures. LEDs, for example, may operate more efficiently at lower temperatures, which may allow the LEDs to output a similar amount of light at a lower level of energy consumption than they would at higher temperatures. Lowered LED temperatures may also result in better overall lifetime of the LEDs, which may result in a longer operating time before the LEDs need to be replaced. Additionally, such cooling of an LED array may allow increased light output from the LEDs without overheating, allowing for increased levels of light and/or disinfection in the room.

As shown in FIG. 1, the light emitting system 100 may comprise a vertically disposed exhaust 102 and exhaust fan 104. The light emitting system 100 may be installed within a ceiling 108, a wall, a range hood, or other similar structure. The exhaust 102 and exhaust fan 104 may be configured to pull air from below (e.g., beneath the ceiling 108) or from outside of the light emitting system 100 and through one or more vents or baffles 110 as shown by the direction of airflow 116. The one or more vents or baffles 110 may be disposed adjacent to a lens 112 where light 113 emitted from the light emitter(s) 106 may pass therethrough. In some examples, the one or more internal flaps, vents, or baffles 110 may be configured to open and/or close manually or using a motor 120. The motor 120 may be controlled by a control system 118, which may open and/or close the one or more vents or baffles based on a user input or programmed to determine when to open and/or close based on sensors and/or user inputs. For example, a control system 118 may operate the vents or baffles 110 to control airflow through the light emitting system 100. The internal flaps may be adjusted, automatically or manually, to change the flow of air within the light emitting system 100. For example, the flaps may be adjusted to move the flow of air further or closer to the light emitter(s) 106.

The light emitter(s) 106 may comprise a heat sink 114 or other heat dissipation elements disposed thereon. In some examples, the substrate 107 may comprise the heat sink 114. The heat sink 114 may be configured to dissipate heat from the light emitter(s) 106. The exhaust 102 and exhaust fan 104 may be configured to pull and/or push air from the vents or baffles 110 and across the heat sink 114 to further dissipate heat generated by the light emitter(s) 106 and dissipated to the heat sink 114. In some examples, the air may be pulled and/pushed across the substrate 107. As shown in FIG. 1, the air may exit the light emitting system 100 through the exhaust 102. The exhaust 102 may be vented, for example, outside of the structure where the light emitting system 100 is mounted. In other examples, the exhaust 102 may be recirculated and the air may be returned to inside the structure where the light emitting system 100 is mounted.

As shown in FIGS. 2A-2B, a light emitting system 200 may comprise a horizontally disposed exhaust 202 and exhaust fan 204. The light emitting system 200 may be installed within a ceiling 208, a wall, a range hood, or other similar structure. The exhaust 202 and exhaust fan 204 may be configured to pull air from below (e.g., beneath the ceiling 208) or from outside of the light emitting system 200 and through one or more vents or baffles 210 as shown by the direction of airflow 216. The one or more vents or baffles 210 may be disposed adjacent to a lens 212 where light 213 emitted from light emitter(s) 206 may pass therethrough. The light emitter(s) 206 may be disposed on a substrate 207. A control system 218 may be used to control the operation of the light emitting system 200. The light emitting system 200 may comprise a motor 220 to adjust the vents or baffles 210. The control system 218 may control light characteristics and/or airflow characteristics of the light emitting system 200 (e.g., the control system 218 may, for example, control the exhaust fan 204, light emitter(s) 206, baffles 210, etc.).

As shown in FIG. 2B, the light emitter(s) 206 may comprise a heat sink 214 or other heat dissipation element disposed thereon to dissipate heat from the light emitter(s) 206. The light emitter(s) 206 may be disposed on a substrate 207. The substrate 207, in some examples, may comprise the heat sink 214 and dissipate heat from the light emitter(s) 206. The exhaust 202 and exhaust fan 204 may be configured to pull and/or push air though the vents or baffles 210 and across the light emitter(s) 206, substrate 207, and/or heat sink 214 to further dissipate heat generated by the light emitter(s) 206. As shown in FIG. 2A, the light emitter(s) 206 may not comprise a heat sink and the exhaust 202 and exhaust fan 204 may be configured to pull and/or push air from the vents or baffles 210 and over the light emitter(s) 206 and/or substrate 207 to dissipate heat generated by the light emitter(s) 206. In the illustrated example of FIG. 2A, the airflow 216 of the light emitting system 200 may effectively replace or reduce the need for the heat sinks 214 (or similar elements) shown in FIG. 2B by dissipating/removing heat from the light emitter(s) 206 with or without the use of heat sinks 214. In some examples, the substrate 207 may effectively replace or reduce the need for a separate heat sink 214. In some examples, the airflow 216 may cool the light emitter(s) 206 by flowing across the side of the substrate 207 opposite the light emitter(s) 206 and dissipating the heat from the light emitter(s) 206 absorbed by the substrate 207. In some examples, heat dissipated from the light emitter(s) 206, to the substrate 207 and/or heat sink 214 may be further dissipated to the rest of the light emitting system 200. The airflow 216 shown in FIGS. 2A-2B may exit the light emitting system 200 through the exhaust 202. The exhaust 202 may be vented, for example, outside of the structure where the light emitting system 200 is mounted. In other examples, the exhaust 202 may be recirculated and the air may be returned to inside the structure (e.g., ceiling, wall, range hood, etc.) where the light emitting system 200 is mounted.

Figure 3:
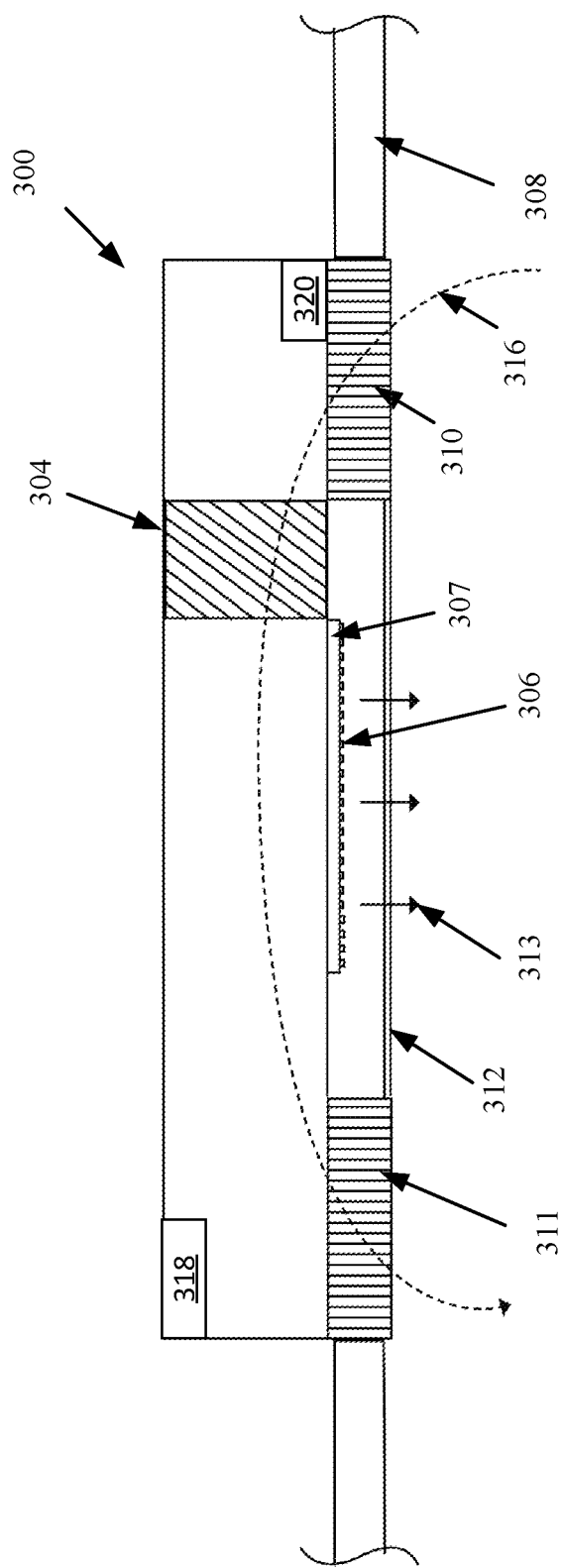
FIG. 3 shows an example light emitting system including a light emitter and a fan system in accordance with an example of the present disclosure.

As shown in FIG. 3, a light emitting system 300 may comprise a horizontally disposed fan 304 without an exhaust. The light emitting system 300 may be installed within a ceiling 308, a wall, a range hood, or other similar structure. The fan 304 may be configured to pull air from below (e.g., beneath the ceiling 308) or from outside (not shown) of the light emitting system 300 through a first baffle 310, propel air over light emitter(s) 306 and associated substrate 307, and propel air out a second baffle 311 (e.g., recirculate the air to below the ceiling 308). The first baffle 310 and the second baffle 311 may be disposed adjacent to a lens 312 where light 313 emitted from light emitter(s) 306 may pass therethrough. The first baffle 310 and/or the second baffle 311 may be opened and/or closed by a motor 320. A control system 318 may control various aspects of the light emitting system (e.g., control the motor 320, fan 304, light emitter(s) 306, etc.). In some examples, the airflow 316 may flow over a back side of the substrate 307, as shown in FIG. 3, and may not come into direct contact with the light emitter(s) 306. In other examples, the airflow may pass directly over the light emitter(s) 306. In the illustrated example of FIG. 3, air may be recirculated back into an environment as shown by the direction of air flow 316. Such air may be filtered, heated based on the heat generated by the light emitter(s) 306, heated with an infrared (IR) heating element, scented, etc.

Figure 4:
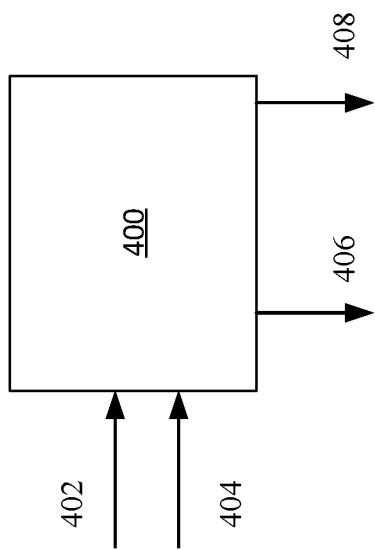
FIG. 4 shows a block diagram of an example light emitting system including a light emitter and an exhaust system in accordance with an example of the present disclosure.

FIG. 4 illustrates a block diagram of the light emitting system 100, 200, 300, 400. As shown in FIG. 4, energy for the exhaust fan 402 may be input into the light emitting system 100, 200, 300, 400. Further, energy for the light emitter(s) 404 may be input into the light emitting system 100, 200, 300, 400.

The light emitting system 400 may output, for example, heat, air, and undesirable airborne particles 406. In some examples, the light emitting system 400 may output heat, air, and undesirable airborne particles 406 outside of the area where the light emitting system 400 is located (e.g., heat, air, and undesirable particles may be vented outside of a room where the light emitting system 400 is mounted). In some examples, heat, air, and undesirable airborne particles 406 may be output into the area where the light emitting system 400 is located (e.g., heat, air, and undesirable particles may be returned to a room where the light emitting system 400 is mounted). In some examples, undesirable airborne particles may be separated (e.g., filtered) from the air and/or heat. Undesirable airborne particles may be output outside of the area where the light emitting system 400 is located and the air and/or heat may output into the area where the light emitting system 400 is located. Radiometric and photometric energy (e.g., disinfecting light) 408 may be output by the light emitting system to provide disinfection.

The light emitting system 100, 200, 300 may be tuned (e.g., by a control system 118, 218, 318) to increase system performance and component lifetime. Increased system performance may correspond to, for example, an increased in light output, reduced energy consumption, reduced heat output, etc. Increased component lifetime, for example, may correspond to an increase in the average lifetime of a component of the light emitting system (e.g., exhaust fan 104, 204, 304 lifetime, light emitter(s) 106, 206, 306, etc.).

The light emitting system 100, 200, 300 may be tuned to reduce overall thermal dissipation system costs. Reduced overall thermal dissipation system costs may correspond to a reduction in energy consumption of the exhaust fan 104, 204, 304 and/or the light emitter(s) 106, 206, 306.

Light emitting system 100, 200, 300 may be capable of providing a spectrum of white light inclusive of a visible light disinfection and may provide increased functionality and safety, e.g., avoiding potential hazards of Ultraviolet C (UVC) germicidal radiation. Many UVC sources may not be heatsinked nor benefit from increased functionality of LED systems. Visible light disinfection utilizing LEDs (as opposed to lamps) may generate excess heat and benefit from forced air exhaust.

The light emitting system 100, 200, 300 may further include a heating element (e.g., an IR lamp or LEDs). The heating element may increase the temperature of the airflow created by the exhaust fan 104, 204, 304. The airflow may be heated by the heating element, before being exhausted to the atmosphere, to increase the temperature of the environment around the light emitting system 100, 200, 300. A disinfection portion of light may operate as an integral component of the white light spectrum(s) at a certain spectral concentration, and may be operable in a mode with only the disinfection portion of the lighting activated.

In some examples, the exhaust fan 104, 204, 304 may be configured to treat (e.g., filter, remove, heat, recirculate, etc.) air without dissipating heat generated by light emitter(s) 106, 206, 306. For example, some LEDs may run cool and may not require extensive heat sinking, such that there may be less need for cooling through air flow. In such examples, the exhaust fan 104, 204, 304 may be utilized with disinfecting light emitter(s) 106, 206, 306 and configured such that the exhaust fan 104, 204, 304 does not dissipate heat from the disinfecting light emitter(s) 106, 206, 306. Such an exhaust fan and disinfection unit may be mounted in many different way and applications, such as, for example, a recessed bathroom fixture, within a range hood, surface mount in a ceiling, etc.

The light emitter(s) 106, 206, 306 may include LEDs, organic LEDs (OLEDs), semiconductor dies, lasers, flexible LEDs, electroluminescent devices, etc. In some examples, two or more light emitters may be disposed with one or more light-converting materials (e.g., phosphors, optical brighteners, quantum dots, phosphorescent materials, fluorophores, fluorescent dyes, conductive polymers, quantum dots, etc.). The one or more light-converting materials may be configured such that at least some of the light emitted from light emitter(s) 106 may be directed into the light-converting material(s). The one or more light-converting materials may be configured to convert at least a portion of light directed into the light-converting material(s) into light having a different quality (e.g., a different peak wavelength). Light may be converted by the light-converting material(s) by absorbing the light, which may energize or activate the light-converting material(s) to emit light of a different quality (e.g., a different peak wavelength). In some examples, the light emitter(s) 106 and the light-converting material(s) may have a proportion of spectral energy measured in an approximately 380 nm to approximately 420 nm wavelength range of greater than approximately 20%. In some examples, a combined light emitted by the light emitter(s) 106 and the light-converting material(s) may be white and may have one or more of the following properties: (a) a proportion of spectral energy measured in an approximately 380 nm to approximately 420 nm wavelength range of greater than approximately 10%, (b) a correlated color temperature (CCT) value of 1000K to 8000K, (c) a color rendering index (CRI) value of 55 to 100, (d) a color fidelity (Rf) value of 60 to 100, and/or (e) a color gamut (Rg) value of 60 to 140.

In some examples, the light emitting system 100, 200, 300 may further include a control system 118, 218, 318 capable of altering the combined light output and/or airflow. The control system 118, 218, 318 may be within, external to, or in communication with light emitting system 100, 200, 300. The control system 118, 218, 318 may include any control system, hardware, software, or a combination thereof, which enables modulation of the combined light output and/or airflow control. For example, the control system 118, 218, 318 may increase or decrease the spectral content of approximately 380-420 nm light. The control system 118, 218, 318 may increase or decrease the emission of light emitted outside of the approximately 380-420 nm range. The control system 118, 218, 318 may also comprise a power supply.

The control system 118, 218, 318 may be used to determine when a desired dose of light has been achieved, and lower the light, turn off the light, or switch to a different lighting mode in response. In order to determine the dose ($J/cm^2$), the control system 118, 218, 318 may determine the irradiance of the light ($mW/cm^2$) and the length of time the light is on. The irradiance of the light may be determined by the radiant flux of the light and the distance between the light emitter(s) 106, 206, 306 and a surface. The control system 118, 218, 318 may be configured to determine the irradiance in accordance with Equation 1 and the dose in accordance with Equation 2. The control system 118, 218, 318 may have the irradiance of light preprogramed into memory based on the radiant flux of the light emitters 106, 206, 306 and an estimated or assumed distance from the light to a surface or wall in the room. The control system 118, 218, 318 may also correlate irradiance to power consumption of the lights. The control system 118, 218, 318 may be in communication with a sensor such as a photodiode or spectrometer to measure irradiance or reflected light (which may then be correlated to irradiance and radiant flux). A photodiode may be used with a filter (e.g., 405 nm bandpass filter) to allow measurement of only disinfecting wavelengths. The control system 118, 218, 318 may keep track of how long light has been on using a timer, counter, real-time clock, polling for the time over a wireless network, or microcontroller system. In some examples, the control system 118, 218, 318 may, based on the timer, counter, real-time clock, polling for the time over a wireless network, or microcontroller system, change a light mode of the light emitting system 100, 200, 300 (e.g., change between a white light disinfection mode and a disinfection only mode).

The control system 118, 218, 318 may include a sensor for detecting internal, external, and changes in characteristics such as temperature to ensure the system runs at or below a desired temperature. The control system 118, 218, 318, based on the sensor information may adjust airflow characteristics or lighting characteristics for the system. In some examples, the control system 118, 218, 318 may detect that the internal temperature within the light emitting system 100, 200, 300 has exceeded a predetermined threshold operating temperature. The control system 118, 218, 318 may adjust the operation of the light emitting system 100, 200, 300 to ensure proper cooling protocols of the light emitter(s) 106, 206, 306. The control system 118, 218, 318 may reduce the light output of the light emitting system 100, 200, 300 to reduce the amount of heat generated by the light emitter(s) 106, 206, 306. The control system 118, 218, 318 may turn off some or all light emitter(s) 106, 206, 306 to reduce the amount of heat created by the light emitting system 100, 200, 300. In some examples, temperature measured by the sensors (e.g., measured temperature) may be the temperature of one of the light emitter(s) 106, 206, 306. In some examples, the measured temperature may be a temperature measured from the substrate 107, 207, 307, such as, for example, measured at the hottest location on the substrate 107, 207, 307. In some examples the measured temperature may be determined elsewhere in the light emitting system 100, 200, 300. The measured temperature may be used by the control system 118, 218, 318 directly, or may be extrapolated to estimate a temperature elsewhere in the light emitting system 100, 200, 300. For example, a measured temperature of the substrate 107, 207, 307 may be extrapolated to estimate the temperature of the light emitter(s) 106, 206, 306 (e.g., LED temperature, LED junction temperature, etc.).

In some examples, the control system 118, 218, 318 may change the flow of air within the light emitting system 100, 200, 300 and/or adjust the intensity of the light emitter(s) 106, 206, 306. The sensor may measure the temperature of the light emitter(s) 106, 206, 306 and the control system 118, 218, 318 may determine if the measured temperature exceeds a threshold operating temperature for the light emitter(s) 106, 206, 306 and the control system 118, 218, 318 may adjust the temperature accordingly (e.g., by adjusting air flow, adjusting fan speed, opening/closing vents or baffles, adjusting light intensity, etc.). The control system 118, 218, 318 may control the flow of air within the light emitting system 100, 200, 300 by controlling the vents, baffles, or internal flaps. The control system 118, 218, 318 may integrate with the vents, baffles, or internal flaps to adjust based on sensor data collected.

Figure 5:
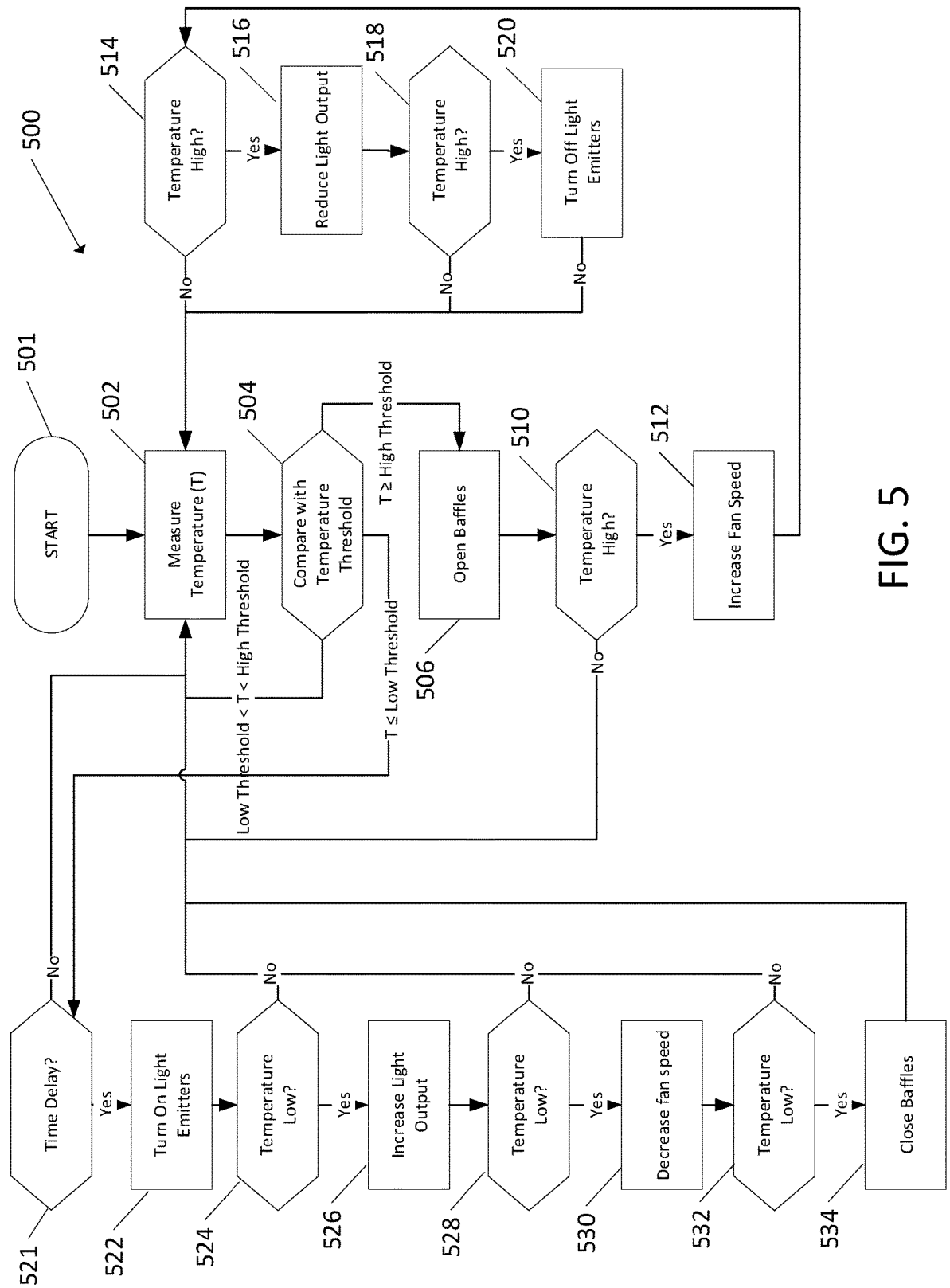
FIG. 5 shows a flow chart for an example control system for a light emitting system including a light emitter and a fan system in accordance with an example of the present disclosure.
Figure 6:
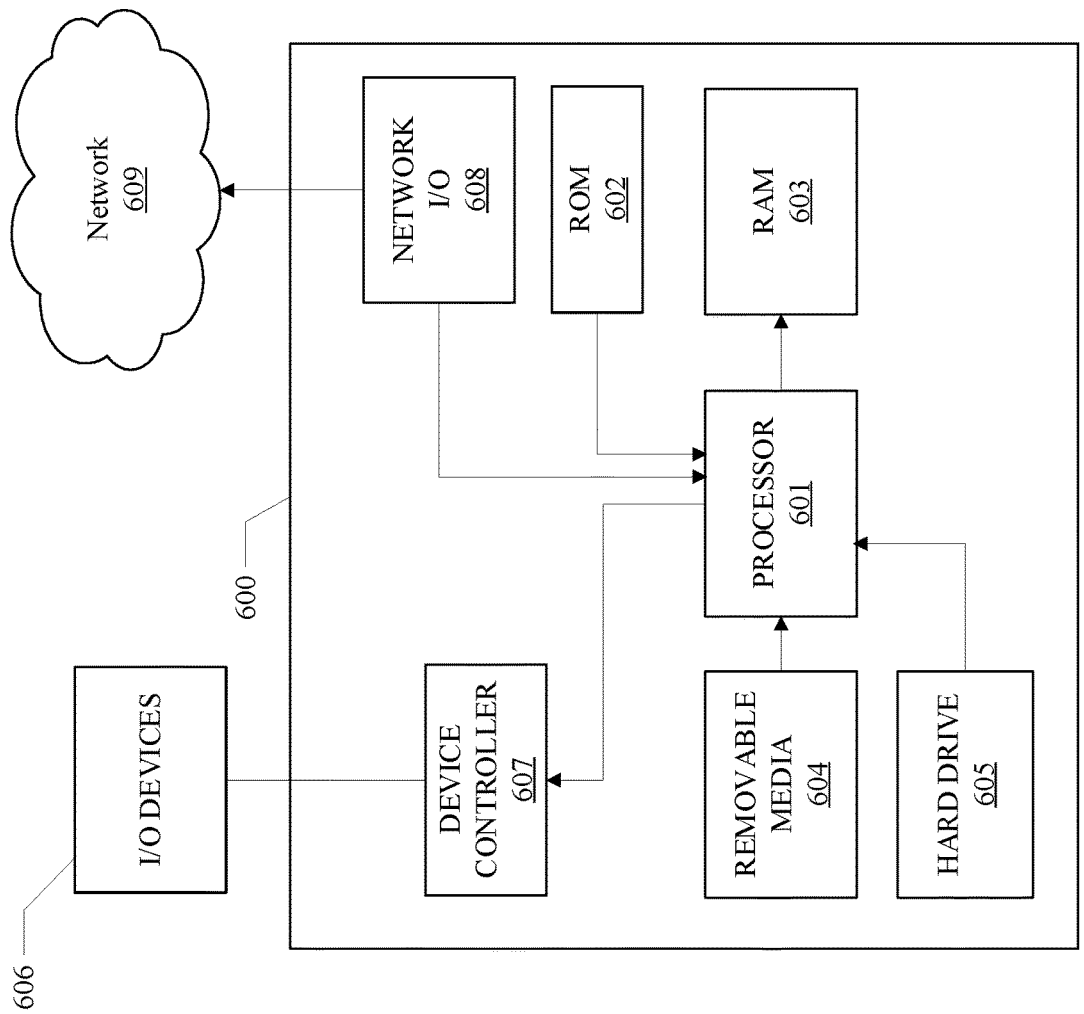
FIG. 6 shows an example hardware platform as may implement features in accordance with examples of the present disclosure.

The control system 118, 218, 318 may, for example, adjust the lighting and airflow characteristics for the light emitting system 100, 200, 300. The control system 118, 218, 318 may perform a combination of reducing the amount of light output from light emitter(s) 106, 206, 306, turning off the light emitter(s) 106, 206, 306, and/or changing the flow of air within the light emitting system 100, 200, 300 to control the temperature of the light emitting system 100, 200, 300. FIG. 5 is a flow chart showing an example process 500 of a control system 118, 218, 318 as may be used with the light emitting system 100, 200, 300. Beginning at step 501, the light emitter(s) 106, 206, 306, for the purpose of discussion of the flow chart, are assumed to be on and turned to the highest output setting, the baffles 110, 210, 310 are assumed to be closed, and the fan 104, 204, 304 is assumed to be off.

The lighting and airflow characteristics may be adjusted by the control system 118, 218, 318 based on the temperature of the light emitting system 100, 200, 300. In some examples, other sensors may be used to provide information to the control system 118, 218, 318 to adjust lighting and airflow characteristics. The control system 118, 218, 318 may measure the temperature (T) of the light emitting system 100, 200, 300 at step 502. The control system 118, 218, 318 may determine if the measured temperature (T) of the light emitting system 100, 200, 300 is at, above, or below a low threshold temperature and a high temperature threshold at step 504.

If the measured temperature (T) is above the low temperature threshold and below the high temperatures threshold (step 504: Low Threshold<T<High Threshold), the control system 118, 218, 318 may continue measuring the temperature (T) of the light emitting system 100, 200, 300 (step 502). A measured temperature (T) that is above the low temperature threshold and below the high temperature threshold may indicate that no adjustment to the airflow or lighting characteristics should be performed.

If the measured temperature (T) is at or above the high threshold temperature (step 504: T≥High Threshold), the control system 118, 218, 318 may open the baffles (step 506) if the baffles are not already opened. The high threshold temperature, for example, may be 55° C. (131° F.) when measured from the substrate 107, 207, 307. The high threshold temperature may vary depending on the application. In other applications, the high threshold temperature may be, for example 85° C. (131° F.), 105° C. (221° F.), or 125° C. (257° F.). In some examples, the baffles may be opened or closed. In some examples, the baffles may be opened by a percentage of the total baffle opening. In some examples, at step 506, the control system 118, 218, 318 may fully open the baffles. In some examples, at step 506, the control system 118, 218, 318 may partially open the baffles. In some examples, at step 506, the control system 118, 218, 318 may fully open baffles that were previously partially opened. If the baffles were already fully opened before step 506, the control system 118, 218, 318 may proceed to step 510.

The control system 118, 218, 318 may determine, after opening the baffles, if the measured temperature (T) is at or above the high temperature threshold (step 510). If the measured temperature (T) is still at or above the high temperature threshold (step 510: YES), the control system 118, 218, 318 may increase the fan speed (step 512). If the measured temperature (T) is not at or above the high temperature threshold, (step 510: NO), the control system 118, 218, 318 may continue measuring the temperature of the light emitting system 100, 200, 300 (step 502). In some examples, the fan may be off before step 512, and the fan may be turned on at step 512. In some examples, the fan may be turned on or off. In some examples, the fan may have a number of speeds that may be adjusted by the control system 118, 218, 318. In some examples, the control system 118, 218, 318, at step 510, may adjust the fan speed based on (e.g., proportional to) the measured temperature (T).

The control system 118, 218, 318 may determine, after increasing the fan speed (step 512), if the measured temperature (T) is still at or above the high temperature threshold (step 514). If the measured temperature (T) is at or above the high temperature threshold (step 514: YES), the control system 118, 218, 318 may reduce the light output of the light emitters (step 516). If the measured temperature (T) is not at or above the high temperature threshold (step 514 NO), the control system 118, 218, 318 may continue measuring the temperature (step 502) of the light emitting system 100, 200, 300. In some examples, reducing the light output of the light emitters, at step 516, may comprise reducing the radiant flux of the light emitters. In some examples, the light emitters, prior to step 516, may be set to the lowest possible light output. If the light emitters are set at the lowest possible light output setting, the control system 118, 218, 318 may proceed to step 518 without reducing the light output.

The control system 118, 218, 318 may determine, after reducing the light output of the light emitters (step 516), if the measured temperature (T) is still at or above the high temperature threshold (step 518). If the measured temperature (T) is still at or above the high temperature threshold (step 518: YES), the control system 118, 218, 318 may turn off one or more of the light emitters (step 520). In some examples, the control system 118, 218, 318 may limit the number of light emitters that can be turned off (e.g., control system 118, 218, 318 may determine that at least one light emitter must remain on). The control system 118, 218, 318 may determine, based on the measured temperature (T), how many light emitters to turn off at step 520. The control system 118, 218, 318 may continue measuring the temperature (step 502) of the light emitting system 100, 200, 300.

Referring back to step 504, the measured temperature (T) may be at or below the low temperature threshold. If the measured temperature (T) is at or below the low temperature threshold (step 504: T≤Low Threshold), the control system 118, 218, 318 may determine if a time delay has been satisfied (step 521). The control system, based on or in response to the time delay, may determine to delay adjusting the airflow and light characteristics when the measured temperature (T) is below the low temperature threshold. The time delay may, for example, allow the light emitters to heat up after being turned on, without adjusting the airflow and lighting characteristics for a determined time period. The control system 118, 218, 318 may determine, based on a time delay, how long the measured temperature (T) has been at or below the low temperature threshold (step 521). If the measured temperature (T) has not been at or below the low temperature threshold for a threshold time period (step 521: NO), the control system 118, 218, 318 may continue measuring the temperature of the light emitting system 100, 200, 300 (step 502). If the measured temperature (T) has been at or below the low threshold temperature for the threshold time period (step 521: YES), the control system 118, 218, 318 may turn on additional light emitters (step 522).

The control system 118, 218, 318 may turn on additional light emitters (step 522) if any of the light emitters are not already on. If all of the light emitters are already on at step 522, the control system 118, 218, 318 may proceed to the next step (step 524) without turning on any light emitters. The control system 118, 218, 318 may determine, after turning on additional light emitters (step 522), if the measured temperature (T) is still at or below the low temperature threshold (step 524). If the measured temperature (T) is still at or below the low temperature threshold (step 524: YES), the control system 118, 218, 318 may increase the light output of the light emitter(s) (step 526), if the light emitter(s) are not already at a maximum output. If the measured temperature (T) is above the low temperature threshold (step 524: NO), the control system 118, 218, 318 may continue measuring the temperature of the light emitting system 100, 200, 300 (step 502).

The control system 118, 218, 318 may determine, after increasing the light output of the light emitters (step 526), if the measured temperature (T) is still at or below the low temperature threshold (step 528). If the measured temperature (T) is still at or below the low temperature threshold (step 528: YES), the control system 118, 218, 318 may decrease the fan speed (step 530) if the fan speed is below the maximum fan speed. In some examples, the control system 118, 218, 318, in step 530, may turn off the fans, decreasing the fan speed to zero. In some examples, the fan may have a number of the different speeds, and the control system 118, 218, 318 may determine how far to decrease the fan speed based on the measured temperature (T). If the fan is already off at step 530, the control system 118, 218, 318 may continue to step 532 without adjusting the fan speed. If the measured temperature (T) is above the low temperature threshold (step 528: NO), the control system 118, 218, 318 may continue measuring the temperature of the light emitting system 100, 200, 300 (step 502).

The control system 118, 218, 318 may determine, after decreasing the fan speed (step 530), if the measured temperature (T) is still at or below the low temperature threshold (step 532). If the measured temperature (T) is still at or below the low temperature threshold (step 532 YES), the control system 118, 218, 318 may close the baffles (step 532) if the baffles are open. In some examples, the baffles may be opened or closed. In some examples, the baffles may be closed by a percentage of the total baffle opening. In some examples, at step 534, the control system 118, 218, 318 may fully close the baffles. In some examples, at step 534, the control system 118, 218, 318 may partially close the baffles. In some examples, at step 534, the control system 118, 218, 318 may fully close baffles that were previously partially closed. If the baffles were already fully closed before step 534, the control system 118, 218, 318 may proceed to step 502.

If the measured temperature (T) is above the low temperature threshold (step 532: NO), the control system 118, 218, 318 may continue measuring the temperature of the light emitting system 100, 200, 300 (step 502). The control system 118, 218, 318, after closing the baffles (step 534), may continue measuring the temperature of the light emitting system 100, 200, 300 (step 502).

The control system 118, 218, 318 may perform any of the steps shown in FIG. 5 in any order and in any combination (e.g., reduce light output (step 516) before increasing fan speed (step 512)). The control system 118, 218, 318 may perform any of the steps shown in FIG. 5 at substantially the same time (e.g., open baffles (step 506) and increase the fan speed (step 512) at the same time). The control system 118, 218, 318 may determine the amount of change in each step based on the measured temperature (T) (e.g., based on the measured temperature, the control system 118, 218, 318, at step 512, may determine the increase in fan speed based on the measured temperature (T)).

The control system 118, 218, 318 may be configured to switch between two different modes of light. The first mode may be a white light mode used for general illumination. The first mode may also be a white light disinfection mode used for general illumination and/or disinfection. A second mode may be a disinfection only mode used primarily for disinfection. The disinfection only mode may emit primarily disinfecting wavelengths used for disinfection. The disinfection mode may primarily emit light in the 380-420 nm wavelength. The disinfection only mode may emit light where at least 20% of the spectral energy is between 380-420 nm. The disinfection only mode may emit light having a peak at 405 nm. Other wavelengths may be added to be used for basic illumination, such as for use as a night light.

The control system 118, 218, 318 may comprise a user interface for allowing for manual user control over the light emitting system 100, 200, 300. Manual user control may supersede, be in addition to, or instead of automated control as is shown in FIG. 5. The control system 118, 218, 318 may comprise a user input (e.g., switch, dial, touchscreen, etc.) for allowing user input to the control system 118, 218, 318. The control system 118, 218, 318, based on user input, may allow for the user to manually update sensor thresholds of the control system 118, 218, 318, such as, for example, the lower temperature threshold or the high temperature threshold. In some examples, the control system 118, 218, 318, based on user input, may turn on or turn off the light emitter(s) 106, 206, 306. In some examples, the control system 118, 218, 318, based on user input, may adjust the output of the light emitter(s) 106, 206, 306.

In some examples, the control system 118, 218, 318, based on user input, may change the light mode of the light emitting system 100, 200, 300 (e.g., change between the white light disinfection mode and the disinfection only mode). In some examples, the control system, 118, 218, 318, based on user input, may set a timer (e.g., manually set an amount of time for the light emitting system to be in a light mode) or a time schedule (e.g., manually set a time schedule based on a time of day). The control system 118, 218, 318 may, based on the timer, change the light mode of the light emitting system 100, 200, 300.

In some examples, the control system 118, 218, 318, based on user input, may turn the exhaust fan 104, 204, 304 on or off. In some examples, the control system 118, 218, 318, based on user input, may adjust the speed of the exhaust fan 104, 204, 304. In some examples, the control system 118, 218, 318, based on user input, may open, close, or otherwise adjust the vents or baffles 110, 210, 310.

The control system 118, 218, 318 disclosed herein may be implemented via a computing device. The computing device may include one or more processors, which may execute instructions of a computer program to perform any of the features described herein. The instructions may be stored in any type of tangible computer-readable medium or memory, to configure the operation of the processor. As used herein, the term tangible computer-readable storage medium is expressly defined to include storage devices or storage discs and to exclude transmission media and propagating signals. For example, instructions may be stored in a read-only memory (ROM), random access memory (RAM), removable media, such as a Universal Serial Bus (USB) drive, compact disk (CD) or digital versatile disk (DVD), floppy disk drive, or any other desired electronic storage medium. Instructions may also be stored in an attached (or internal) hard drive. The computing device may include one or more input/output devices, such as a display, touch screen, keyboard, mouse, microphone, software, user interface, etc. The computing device may include one or more device controllers such as a video processor, keyboard controller, etc. The computing device may also include one or more network interfaces, such as input/output circuits (such as a network card) to communicate with a network such as example network. The network interface may be a wired interface, wireless interface, or a combination thereof. One or more of the elements described above may be removed, rearranged, or supplemented without departing from the scope of the present disclosure.

Light emitted by the light emitter(s) 106, 206, 306 and the light-converting material(s) may be modified by optics, reflectors, or other assembly components. In some example, the light emitted by the light emitter(s) 106, 206, 306 and light-converting material(s) may be modified by the optics, reflectors, or other assembly components to improve visual light quality, such as, for example, to facilitate the combined light emitted by the light-emitting device being perceived as white or a hue of white. Diffusers, reflectors, optics, protective shields, and other transmissive components of a light fixture or light bulb may contribute significantly to the overall efficiency of product function. While these materials may not have 100% transmission or reflection efficiency, the choice of material(s) may be of value in lighting design to obtain high efficiencies for an effective and efficient product. Many plastics, glasses, coatings, and other materials may be acceptable for reflectors or transmissive components (e.g., diffusers) for general illumination sources, such as incandescent bulbs, fluorescent bulbs, and RGB/phosphor converted blue pump LEDS. These lighting sources may rely little on near-UV wavelengths in product function.

Many of these reflectors or transmissive components may exhibit a sharp drop off in reflectance or transmission efficiency (sometimes close to zero) for wavelengths of light in the near-UV range, e.g., approximately 380 to approximately 420 nm range. Thus, light sources in which light in the approximately 380 to approximately 420 nm range may be a component of the illumination that can show significant losses with some reflective or transmissive materials in light bulb or light fixture design. Reflector and transmissive materials may be selected appropriately based on the output of light from a light source.

In examples where a light contains a significant proportion of approximately 380 to approximately 420 nm light, the light emitting system 100, 200, 300 may comprise reflective surfaces or reflector optics that have less than approximately 70% loss of energy after a single reflectance of light in the approximately 380 to approximately 420 nm range. In some examples, a solid transmissive material may have less than approximately 30% loss of energy after transmission of light in the approximately 380 to approximately 420 nm range. In some examples, the portion of light in the approximately 380 to approximately 420 nm range may be sufficient to illuminate an object outside of the fixture with at least approximately 0.05 mW/cm$^2$ of light in the approximately 380 to approximately 420 nm range.

In examples where the light emitter(s) 106, 206, 306 comprise an LED or combination of LEDs, an LED or a combination of LEDs and other light sources (e.g., phosphors, lasers), or a laser diode, the reflective material may be positioned (directly or indirectly) in the path of light from the light emitter(s) 106, 206, 306. The reflective material may be used for the mixing of light, the reflective material may be used to control the distribution of light, or the transmissive material may be used as a lens, a diffuser, an optical component, as a cover or protective shield, and/or to control the distribution of light. In some examples, any reflector or diffuser should include a material that will allow the most approximately 380-420 nm light to emit, and may include any material capable of not substantially absorbing light in the 380 nm to 420 nm range. This material may include plastics, glass, resins, thermoplastic resins, or polymers which may not substantially absorb light in a range of 380 nm to 420 nm.

The light emitters, reflective optics, or transmissive materials may have a coating of Titanium Dioxide ($TiO_2$) or anatase Titanium Dioxide. $TiO_2$ may be used as a photocatalyst when excited by UV or near-UV light, such as 380-420 nm light. This process may increase the rate that organic compounds break down through oxidation. For example, it may be effective at eliminating volatile organic compounds (VOCs), various types of bacteria, and viruses. Photocatalysis may be used with or in lieu of LED lighting and disinfection systems for increased effectiveness.

As further described herein, the control system 118, 218, 318 of FIGS. 1-3 may be implemented by example computing device 600 of FIG. 22. The example devices and systems described herein may be implemented via a hardware platform such as, for example, the example computing device 600 illustrated in FIG. 22. In some examples, the computing device 600 may implement the flowcharts of FIG. 5. The example devices and systems described herein may be separate components, may comprise separate components, or may be incorporated into a single device. Some elements described with reference to the computing device 600 may be alternately implemented in software. The computing device 600 may include one or more processors 601, which may execute instructions of a computer program to perform any of the features described herein. The instructions may be stored in any type of tangible computer-readable medium or memory, to configure the operation of the processor 601. As used herein, the term tangible computer-readable storage medium is expressly defined to include storage devices or storage discs and to exclude transmission media and propagating signals. For example, instructions may be stored in a read-only memory (ROM) 602, random access memory (RAM) 603, removable media 604, such as a Universal Serial Bus (USB) drive, compact disk (CD) or digital versatile disk (DVD), floppy disk drive, or any other desired electronic storage medium. Instructions may also be stored in an attached (or internal) hard drive 605. The computing device 600 may include one or more input/output devices 606, such as a display, touch screen, keyboard, mouse, microphone, software user interface, etc. The computing device 600 may include one or more device controllers 607 such as a video processor, keyboard controller, etc. The computing device 600 may also include one or more network interfaces 608, such as input/output circuits (such as a network card) to communicate with a network 609. The network interface 608 may be a wired interface, wireless interface, or a combination thereof. One or more of the elements described above may be removed, rearranged, or supplemented without departing from the scope of the present disclosure.

In some examples, a light emitting device for inactivating microorganisms may comprise a vent configured to allow air to flow therethrough. The light emitting device may comprise a light emitter disposed on a substrate and configured to at least produce a light comprising a radiant flux sufficient to initiate inactivation of microorganisms, wherein at least 20% of a spectral energy of the light is in a wavelength range of 380-420 nanometers (nm). The light emitting device may comprise a fan configured to create an airflow through the vent and towards the substrate.

In some examples, the airflow may cool the light emitter.

In some examples, a heat sink may be configured to absorb heat from the light emitter. The airflow may be configured to dissipate heat from the heat sink.

In some examples, to create the airflow, the fan may be configured to pull air over the light emitter.

In some examples, the light may comprise a peak wavelength of 405 nm.

In some examples, the light emitter may be a first light emitter and the light is a first light. The light emitting device may further comprising a second light emitter configured to produce a second light having a wavelength in a range of 380-750 nm. A controller may be in communication with the first light emitter and the second light emitter and configured to switch between a first light mode and a second light mode. The first light mode may comprise emission of the first light and the second light mode may comprise emission of the second light.

In some examples, a light emitting system may comprise a light source configured to emit a light comprising at least 20% of a spectral energy of the light in a wavelength range of 380-420 nanometers (nm) and a radiant flux sufficient to initiate inactivation of microorganisms. The light emitting system may comprise a fan configured to create an airflow through the light emitting system. The light emitting system may comprise a sensor configured to measure a temperature associated with the light source. The light emitting system may comprise a controller in communication with the light source, the fan, and the sensor. The controller may be configured to adjust, based on the temperature associated with the light source, an airflow characteristic.

In some examples, the light source may be a first light source and the light may be a first light. The light emitting system may further comprise a second light source configured to emit a second light having a wavelength in a range of 380-750 nm.

In some examples, the controller may be further configured to adjust, based on the temperature associated with the light source, a light characteristic by switching between a first light mode and a second light mode. The first light mode may comprise emission of the first light and the second light mode may comprise emission of the second light.

In some examples, the controller may be configured to determine an amount of time the light emitting system has been in the first light mode or the second light mode. The controller may switch between the first light mode and the second light mode based on the amount of time the light emitting system has been in the first light mode or the second light mode or a time of day.

In some examples, the controller may be further configured to adjust, based on the temperature associated with the light source, a light characteristic by adjusting a light output of light source.

In some examples, the controller may be configured to adjust the airflow characteristic by adjusting a speed of the fan, and wherein the airflow cools the light source.

In some examples, the light emitting system may comprise a vent. The fan may be configured to enable the airflow to flow through the vent. The controller may be configured to adjust the airflow characteristic by adjusting the vent.

In some examples, the light may comprise a peak at 405 nm.

In some examples, a method may comprise outputting, via a light emitter, a light comprising at least 20% of a spectral energy of the light in a wavelength a range of 380-420 nanometers (nm) and a radiant flux sufficient to initiate inactivation of microorganisms. The method may comprise sensing, via a sensor, a temperature associated with the light emitter. The method may comprise adjusting, based on the temperature associated with the light emitter, an output of the light emitter. The method may comprise adjusting, based on the temperature associated with the light emitter, an airflow created by a fan.

In some examples, the adjusting the output of the light emitter may further comprise reducing, based on determining that the temperature associated with the light emitter exceeds a threshold temperature, the output of the light emitter.

In some examples, the adjusting the output of the light emitter may further comprise turning off, based on determining that the temperature associated with the light emitter exceeds a threshold temperature, the light emitter.

In some examples, the adjusting the airflow created by the fan may further comprise increasing, based on determining that the temperature associated with the light emitter exceeds a threshold temperature, a speed of the fan.

In some examples, the method may further comprises adjusting, based on the temperature associated with the light emitter, a vent. The airflow may be configured to flow through the vent.

In some examples, the adjusting the vent may comprise opening, based on determining that the temperature associated with the light emitter exceeds a threshold temperature, the vent.

The above disclosure is by way of example. Modifications may be made as desired for different implementations. For example, steps and/or components may be subdivided, combined, rearranged, removed, and/or augmented; performed on a single device or a plurality of devices; performed in parallel, in series; or any combination thereof. Additional features may be added.

We claim:

1. A light emitting device for inactivating microorganisms, the light emitting device comprising:
   a baffle configured to allow air to flow therethrough;
   a horizontally disposed exhaust;
   a light emitter positioned above the baffle and disposed on a substrate and configured to at least produce a light comprising a radiant flux sufficient to inactivate microorganisms, wherein at least 20% of a spectral energy of the light is in a wavelength range of 380-420 nanometers (nm);
   a horizontally disposed fan positioned above the baffle and coupled to the exhaust; and
   a heat sink configured to absorb heat from the light emitter, wherein the heat sink is positioned above the light emitter and having a length extending axially aligned with the fan and exhaust, and wherein the fan is configured to pull air from below the baffle, propel the air over the light emitter and heat sink, and propel the air out the exhaust in a direction perpendicular to the air entering the baffle.

2. The light emitting device of claim 1, wherein the airflow cools the light emitter.

3. The light emitting device of claim 1, further comprising a heat sink configured to absorb heat from the light emitter, wherein the airflow is configured to dissipate heat from the heat sink.

4. The light emitting device of claim 1, wherein to create the airflow, the fan is configured to pull air over the light emitter creating a vertical airflow from a bottom of the light emitter to a top of the light emitter and through the fan.

5. The light emitting device of claim 1, wherein the light comprises a peak wavelength of 405 nm.

6. The light emitting device of claim 1, wherein the light emitter is a first light emitter and the light is a first light, the light emitting device further comprising:
   a second light emitter configured to produce a second light having a wavelength in a range of 380-750 nm; and
   a controller in communication with the first light emitter and the second light emitter and configured to switch between a first light mode and a second light mode, wherein the first light mode comprises emission of the first light and the second light mode comprises emission of the second light.

* * * * *